(12) United States Patent
Majeed et al.

(10) Patent No.: US 7,378,442 B1
(45) Date of Patent: May 27, 2008

(54) CHEMICAL ENTITIES WITH MULTIPLE MODES OF ANTI-INFLAMMATORY ACTION

(75) Inventors: Muhammed Majeed, Piscataway, NJ (US); Kalyanam Nagabushnam, Piscataway, NJ (US); Rajendran Ramanujam, Bangalore (IN); Subbalakshmi Prakash, Piscataway, NJ (US)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 11/871,253

(22) Filed: Oct. 12, 2007

Related U.S. Application Data

(62) Division of application No. 11/684,631, filed on Mar. 11, 2007.

(51) Int. Cl.
*A61K 31/315* (2006.01)
*A61K 31/121* (2006.01)

(52) U.S. Cl. .................... 514/513; 514/506; 514/510

(58) Field of Classification Search ............... 514/513, 514/510, 506
See application file for complete search history.

(56) References Cited

U.S. PATENT DOCUMENTS

2005/0123536 A1* 6/2005 Law et al. ............... 424/141.1
2005/0180972 A1* 8/2005 Wahl et al. ............... 424/144.1

* cited by examiner

*Primary Examiner*—Elvis O Price

(57) ABSTRACT

The invention relates to methods of treatment and pharmaceutical compositions of new chemical compounds that inhibit the various enzymes in the arachidonic acid pathway implicated in inflammatory disease conditions.

4 Claims, No Drawings

CHEMICAL ENTITIES WITH MULTIPLE MODES OF ANTI-INFLAMMATORY ACTION

This application is a divisional of U.S. patent application Ser. No. 11/684,631 filed on Mar. 11, 2007.

BACKGROUND INFORMATION

The present invention relates to the multiple modes of inhibition by a drug molecule of an enzymatic pathway postulated for a disease state. In particular the invention relates to new chemical compounds that inhibit the various enzymes in the arachidonic acid pathway implicated in inflammatory disease conditions.

Arachidonic acid is present in cell membranes as esters of phosphorylated glycerides, the so-called phospholipids. Under some defined biological stimulus, certain lipases can hydrolyze, either directly or in stepwise fashion, these phosphorylated arachidonic glycerides to release free arachidonic acid. Of the lipases that perform such function, most preeminent is the enzyme Phopholipase A2; This enzyme hydrolyzes the phospholipids and arachidonic acid is released in a single step.

Once arachidonic acid is released into the cell constituents, there are abundant opportunities for it to undergo transformation into several products. There are five major pathways that regulate the fate of arachidonic acid.

The first pathway is reincorporation of arachidonic acid back onto phospholipids mediated by a group of enzymes including arachidonoyl-CoA synthetase and arachidonoyl-CoA:lysophospholipid transferase;

The second pathway is the transformation of arachidonic acid into pro-inflammatory prostaglandins. Such a transformation is brought about by a group of enzymes called cycloxygenases which are further subdivided mainly into cyclooxygenase-1 and Cycloxygenase-2. While the former is understood to be a constitutive enzyme, the latter is inducible. This pathway generates pro-inflammatory prostaglandins. By inhibition of cyclooxygenase enzymes by suitable substrates, one can exert remedial action of inflammatory reactions. There are several types of anti-inflammatory compounds designed to inhibit cycloxygenases some of them being more selective for Cox-2 than for Cox-1. Foremost among them are the so-called NSAIDs (Non-steroidal anti-inflammatory drugs) have been recognized to be safe over extended periods of usage. Drug molecules like Ibuprofen and Naproxen are among the prominent members of this class of drugs. Several of them belong to the aryl propionic acid structural types.

The third pathway is mediated by lipoxygenases which transform arachidonic acid into hydroperoxy-eicosatetraenoic acids (HPETE). Of the three lipoxygenases (5-LO, 12-LO, 15-LO), the most prominent is 5-Lipoxygenase pathway leading to the formation of leukotrienes. Zileuton is an example of 5-lipoxygenase inhibitor, belonging to the N-hydroxyurea class of compounds. 5-Lipoxygenase operates in a much more complex way. For 5-lipoxygenase to be effective, it needs the cofactors $Ca^{2+}$, ATP and another protein nicknamed 5-FLAP (5-Lipoxygenase activating protein), a membrane protein. 5-Lipoxygenase relocates to the membrane binding with the three cofactors mentioned and starts the transformation of arachidonic acid eventually to result in leukotrienes. Inhibitors of the 5-FLAP are effective anti-inflammatory compound switching off the 5-lipoxygenase chain. Among the 5-FLAP inhibitors may be mentioned, MK-866, (±)2-fluoro-a-methyl-1,1'-Biphenyl]-4-acetic acid. (Novel Inhibitors of Leukotriene, Edited by G. Folco, B, Samuelson, R. C. Murphy, Birkhläuser Verlag, Basel, 1999)

The fourth pathway is again a metabolic one, for example, happening in neural cells where cytochrome $P_{450}$ converts arachidonic acid into an epoxide, Epoxyeicosatrienoic acid which further is converted to diols through the agency of epoxide hydrolases. Similar type of oxidative transformations also occur with other family members of The fifth pathway is diffusion of arachidonic acid outside the cell.

Finally arachidonic acid can also be transformed into its ethanol amide, called Anadamide, identified as an endogenous ligand for cannabinoid receptors in brain cells.

The present invention is designed to inhibit the two major pathways of arachidonic acid, namely cyclooxygenase pathway and 5-Lipoxygenase pathway. Since these two pathways lead pro-inflammatory compounds, simultaneous inhibition of such pathways will lead to enhance efficacy of compounds. By designing suitable compounds which will inhibit both the enzymes, the objectives of reducing inflammatory responses are achieved.

The present invention aims towards synthesis of two molecules connected by a molecular tether in such a way that the tether can be removed by enzymes such as proteolytic enzymes or esterases present in the cell cycloplasm or outside of it. Even with the tether in tact on the molecule, the molecules are configured to inhibit the individual intended enzymes. Boswellic acids have been known to be 5-lipoxygenase inhibitors through a non-redox route. The invention relates to the synthesis of molecules wherein the molecular components are brought together by linkages that can cleave by endogenous enzymes such as proteases, esterase and other hydrolytic enzymatic interventions.

3-Acetyl-11-keto-β-boswellic acid (AKBBA) whose structure is shown below is a potent 5-lipoxygenase inhibitor. It contains a free carboxylic group. The invention described herein transforms the free carboxylic group into a halomethyl ester, in particular to the chloromethyl ester. Such an ester, whose structure is shown within this application, serves as anchor for attaching other potent drug molecules such as Ibuprofen and Naproxen. The choice is not limited to these two only. Other arylpropionic acids can be linked as effectively as these two compounds 3-Acetyl-11-keto-β-boswellic acid (AKBBA)

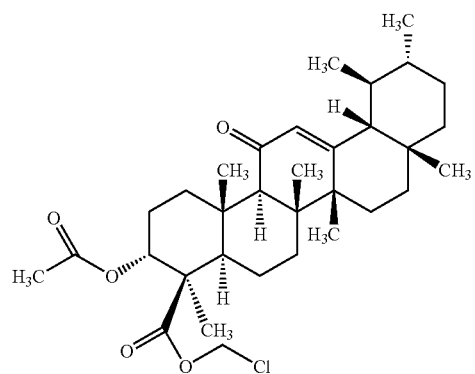

3-O-Acetyl-9,11-dehydro-β-boswellic acid chloromethyl ester

In a variant of this general strategy, Boswellic acids in general can be transformed into other active esters also;

Another variation is represented by the active ester incorporating Boswellic acid diene structure represented herein.

Examples are given below to illustrate the synthesis of such compounds. The examples serve as model ones and do not limit the types of structures that can be prepared by adopting this general strategy

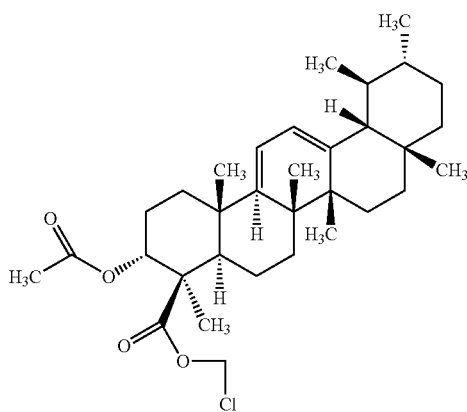

3-Acetyl-β-boswellic acid-9,11-diene-chloromethyl ester

None of such active esters have been described in prior art. Such core structures possess the structural features for 5-Lipoxygenase inhibition. These active sters are condensed with cyclooxygenase inhibiting structures such as arylpropionic acid molecules.

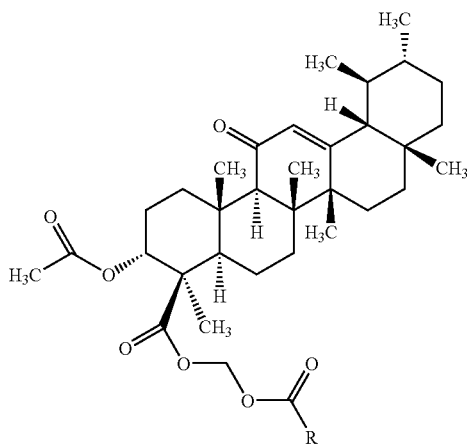

In the structure 'R' represents the core structure of a cyclooxygenase inhibiting features

EXAMPLE 1

3-Acetyl-11-keto-β-boswellic acid chloromethyl ester: AKBBA (1.0 g) in 20 ml of acetone was taken. Under stirring was added 1:2 moles (calculated with respect to AKBBA) of potassium carbonate followed by 1:1.5 moles of Chloroiodomethane. The reaction mixture was heated to reflux and maintained for 15 hrs. TLC was checked for the completion of the reaction. On completion, the mass was cooled to RT and 50 ml of chloroform and 50 ml of water were added to the reaction mass. The reaction mass was stirred well for 15 mts. Chloroform layer was separated and washed with water twice. The organic was dried layer and removed under vacuum to get the crude product which was purified t by column chromatography.

TLC showed two prominent bands. The faster moving band is chloromethyl ester and the slower one is dimer. Both compounds were characterized by NMR and elemental analyses; $C_{33}H_{49}C_{10}C_5$ Calc C, 70.63H, 8.80. Found C, 70.25; H, 8.74.

Yield: 150 mg; Melting point: 232-235° C.

The AKBBA dimer (two molecules of AKBBA bridged by a methylene group) was obtained from the above reaction by column chromatography as a slower moving spot from the column; $C_{65}H_{96}O_{10}$ Calc C, 75.25; H, 9.33. Found C, 75.06; H, 9.33.

Yield: 550 mg; Melting point: 208-212° C.

EXAMPLE 2

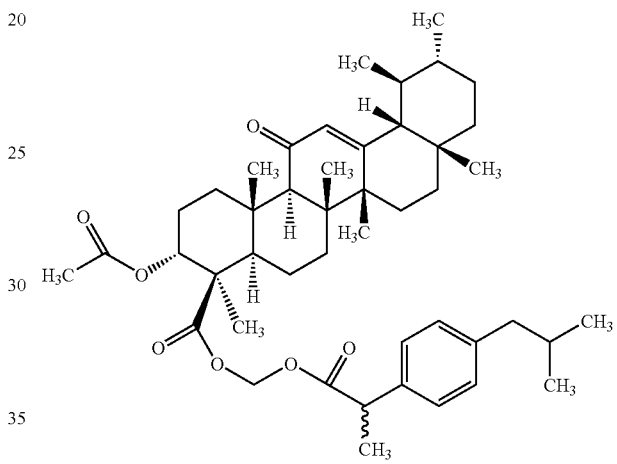

AKBBA-Ibuprofen conjugate: AKBBA chloromethyl ester (400 mg) in 10 ml of acetone along with 1:3 moles of Ibuprofen and 1:2 moles of Potassium carbonate were taken. The reaction mixture was stirred and heated to reflux temperature and maintained for 20 hrs. Checked TLC for the completion of the reaction. The mass was cooled to RT and 25 ml of water and 50 ml of chloroform were added. Stirred for 30 mts. The chloroform layer was separated and washed with water twice (2×50 ml). It was dried over sodium sulfate and removed under vacuum. The product was purified by column chromatography and characterized by NMR and elemental analysis. Since dl-Ibuprofen was used, two diastereomers were detected by NMR; $C_{46}H_{66}O_7$ Calc C, 75.58; H, 9.10. Found C, 75.40; H, 9.19.

Yield: 150 mg; Melting point: 90-95° C.

EXAMPLE 3

3-O-Acetyl-9,11-dehydro-β-boswellic acid chloromethyl ester: 3-Acetyl-β-boswellic acid-9,11-diene (2.5 g, ABBA diene) was taken in 50 ml of acetone and added 1:2 moles of potassium carbonate and stirred for 2 hrs at RT. Then added 1:15 moles of bromochloromethane to the mass and stirred at RT for 50 hrs. Checked TLC for the completion of the reaction. TLC showed the absence of the starting material. Two prominent bands were seen in the TLC with chloromethyl ester around 80% and dimer around 20%. Methylenedichloride (50 ml) was added to the mass under stirring followed by 50 ml of water. Stirred for 1 hr. and Separated the MDC layer, washed with water twice. The organic layer was dried over sod.sulfate and MDC was removed under vacuum. The crude product is purified by column chromatography. $C_{33}H_{49}C_{10}C_4$ Calc C, 72.70; H, 9.06. Found C, 72.89; H, 8.94.

Yield: 1.5 gms. Melting point: 184-186° C.

The dimeric molecule was obtained as a slower moving component in column chromatography; $C_{65}H_{96}O_8$ Calc C, 77.65; H, 9.62. Found C, 77.58; H, 9.60.

Yield: 600 mg; Melting point: 180-182° C.

EXAMPLE 4

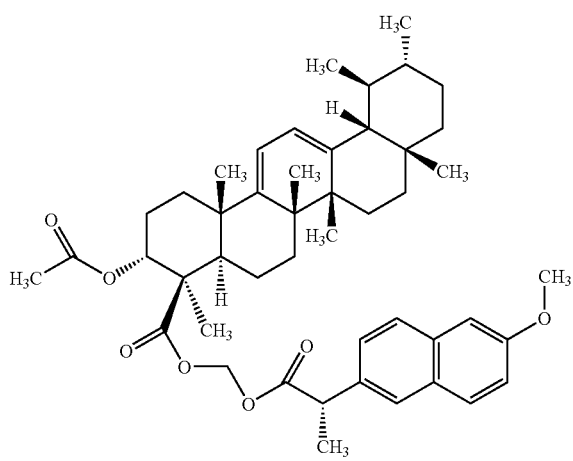

3-O-Acetyl-9,11-dehydro-β-boswellic acid-Naproxen conjugate: To ABBA diene chloromethyl ester (500 mg) in 20 ml of acetone was added 1:2 moles of potassium carbonate and 1:2 moles of S-Naproxen. Stirred the mass well. It was then heated to 50-55° C. and maintain for 15 hrs. TLC was checked for the completion of the reaction. To the reaction mixture were added 50 ml of chloroform and 50 of water and stirred well for 30 mts. The chloroform layer was separated and washed with water twice, dried over sodium sulfate. The solvent was removed under vacuum to get the crude product. The crude product was purified by column chromatography. $C_{47}H_{62}O_7$ Calc C, 76.39; H, 8.46. Found C, 76.29; H, 8.42. Yield: 500 mg Melting point: 105-108° C.

EXAMPLE 5

Comparative anti-inflammatory, antinociceptive and immunomodulatory activities of compounds wherein 3-acetyl-11-keto-β-boswellic acid is linked by a methylene bridge with Ibuprofen (SA-040) or Naproxen (SA-041), and the unmodified compounds Ibuprofen (I), Naproxen (N) and 3-acetyl-11-keto-β-boswellic acid (AKBBA)

Freund's adjuvant (FA) arthritis was induced in rats by a single intraplantar injection into the right hindpaw of 100 microl of *Mycobacterium butirricum* (6 mg/mL). The effect of equimolar doses of the test compounds (1, 3 and 10 mg/kg) was evaluated using two dosage regimen protocols: (i) preventive, starting oral administration of the drugs at the time of induction of arthritis and for the following 21 days (day 1-21); (ii) therapeutic, starting oral administration of the drugs 7 days after adjuvant injection and for the following 14 days (day 7-21).

Hindpaw swelling (days 3, 7, 11, 14, 17, 21) and nociception (days 15 and 21) were measured. On day 22 rats were sacrificed, draining lymph nodes were removed and T cells isolated. In vitro proliferation of T cells following stimulation with concanavalin A (0.5-5 mcg/mL) was measured using a tritiated thymidine incorporation assay.

IL-2 receptor expression on T cells was measured by FACS analysis. SA-040 and SA-041 showed similar activity in reducing oedema formation in the non-injected (controlateral) hindpaw. Both drugs showed anti-nociceptive effect. Both were anti-nociceptive at a dose of 5.9 mg/kg and 5.2 mg/kg while I and N showed the same extent of inhibition only at a dose of greater than 10 mg/kg. T cells were isolated and characterized by FACS analysis. Stimulation of isolated T cells with concanavallin A in vitro caused a significant increase in thymidine uptake. All compounds inhibited T-cell proliferation. The order of activity was SA-041>SA-040>N>1>AKBBA.

What is claimed is:

1. A method for treating a mammal with an inflammatory condition which comprises administering to said mammal an antiinflammatory effective amount of a compound wherein 3-acetyl-9,11-keto-β-boswellic acid is linked by a methylene bridge with a chemical entity selected from Ibuprofen, Naproxen, Ketoprofen, Acetylsalicylic acid, Indomethacin, Carprofen, Fenbufen, Fenoprofen, Flurbiprofen, Loxoprofen, Tiaprofenic acid, Suprofen, Diclofenac, Piroxicam, Phenylbutazone, Nimesulide.

2. A method for treating a mammal with an inflammatory condition which comprises administering to said mammal an antiinflammatory effective amount of a compound wherein 3-O-acetyl-9,11-dehydro-β-boswellic acid is linked by a methylene bridge with a chemical entity selected from Ibuprofen, Naproxen, Ketoprofen, Acetylsalicylic acid, Indomethacin, Carprofen, Fenbufen, Fenoprofen, Flurbiprofen, Loxoprofen, Tiaprofenic acid, Suprofen, Diclofenac, Piroxicam, Phenylbutazone, Nimesulide.

3. A pharmaceutical composition for the treatment of inflammatory conditions which comprises an antiinflammatory effective amount of compounds according to claim 1 or their pharmaceutically acceptable salts together with a pharmaceutically acceptable carrier.

4. A pharmaceutical composition for the treatment of inflammatory conditions which comprises an antiinflammatory effective amount of compounds according to claim 2 or their pharmaceutically acceptable salts together with a pharmaceutically acceptable carrier.

* * * * *